United States Patent [19]
Yn

[11] Patent Number: 5,597,488
[45] Date of Patent: Jan. 28, 1997

[54] METHOD FOR PREPARING VARIOUS THERMAL WATERS

[76] Inventor: Kye-Whan Yn, P.O. Box 137-130, Seoul, Rep. of Korea

[21] Appl. No.: 545,279

[22] Filed: Oct. 19, 1995

Related U.S. Application Data

[63] Continuation-in-part of Ser. No. 335,141, Nov. 7, 1994, abandoned.

[51] Int. Cl.$^6$ ........................................................ C02F 1/42
[52] U.S. Cl. ........................... 210/663; 210/749; 210/765
[58] Field of Search .................... 210/175, 177, 210/181, 182, 194, 195.1, 196, 199, 202, 205, 206, 259, 266, 282, 287, 663, 687, 664, 749, 764, 765, 766, 744, 121, 123–125

[56] References Cited

U.S. PATENT DOCUMENTS

| | | | |
|---|---|---|---|
| 3,215,626 | 11/1965 | Console | 210/57 |
| 3,785,492 | 1/1974 | Mazza | 210/149 |
| 3,817,308 | 6/1974 | Bundo | 159/48 R |
| 3,932,578 | 1/1976 | Nishino et al. | 264/331 |
| 4,115,267 | 9/1978 | Bachhofer et al. | 210/136 |
| 4,325,975 | 4/1982 | Lindon et al. | 426/66 |
| 4,368,123 | 1/1983 | Stanley | 210/269 |
| 4,501,661 | 2/1985 | Karasawa | 210/223 |
| 4,707,263 | 11/1987 | Nishimori et al. | 210/484 |
| 4,732,674 | 3/1988 | Tamura et al. | 210/266 |
| 4,786,420 | 11/1988 | Dalessandro | 210/791 |
| 4,787,973 | 11/1988 | Ando et al. | 210/282 |
| 4,859,345 | 8/1989 | Inagaki | 210/764 |
| 5,006,257 | 4/1991 | Lamothe | 210/650 |
| 5,034,138 | 7/1991 | Hatanaka et al. | 210/749 |
| 5,152,900 | 10/1992 | Sekiguchi et al. | 210/644 |
| 5,174,901 | 12/1992 | Smith | 210/652 |
| 5,215,659 | 6/1993 | Ando | 210/282 |
| 5,277,802 | 1/1994 | Goodwin | 210/202 |

*Primary Examiner*—Cynthia L. Nessler
*Attorney, Agent, or Firm*—Faegre & Benson

[57] ABSTRACT

A method for preparing artificial thermal water suitable to be used as domestic thermal water. In order to prepare the thermal water, a plurality of chemical components are mixed with highly pure water at predetermined rates to prepare a thermal water solution having components similar to those of a natural sodium bicarbonated spring, a simple thermal spring, a carbon dioxide spring, a radioactive spring or a sulfur spring. Fresh water or city water passes in order through an activated carbon filter, a microfilter, a anion-exchange resin and a cation-exchange resin to prepare pure water. The thermal water solution is mixed with the pure water and heated to prepare the thermal water prior to distributing the thermal water to a bathtub.

6 Claims, 2 Drawing Sheets

METHOD FOR PREPARING VARIOUS THERMAL WATERS

CROSS-REFERENCE TO RELATED APPLICATION

This is a continuation-in-part application of application Ser. No. 08/335,141, filed Nov. 7, 1994, now abandoned entitled DEVICE AND METHOD FOR PREPARATION OF THERMAL WATERS.

BACKGROUND OF THE INVENTION

1. Field of the Invention

The present invention relates in general to the preparation of thermal water and, more particularly, to a method for preparing various artificial thermal waters by adding principal mineral ingredients of thermal water to pure water prepared by passing fresh water through both an activated carbon filter and a microfilter to filter off any impurities and in turn treating the filtered water with a pure water preparing device having ion-exchange resin.

2. Description of the Prior Art

Thermal water is hot underground water having not only a temperature exceeding a predetermined temperature level, but also containing principal mineral ingredients therein. Thermal water is particularly used as bath water since thermal water is good for both health and beauty due to its ingredients.

However, using natural thermal water is inconvenient because of the geographical location of the spa and the great expense in developing the natural thermal water. In this regard, it is difficult to increase the popularity of natural thermal water.

SUMMARY OF THE INVENTION

It is, therefore, an object of the present invention to provide a method for preparing artificial thermal water in which the above problems caused in using natural thermal water can be overcome and which readily prepares good artificial thermal water having optimal quality suitable to be used in a hot spring cure and thereby allowing people quick use of the thermal water for domestic bath water.

In order to accomplish the above object, the present invention provides a method for preparing thermal water comprising the steps of:

mixing a plurality of chemical components with highly pure water at predetermined rates to prepare a thermal water solution having components similar to those of a natural sodium, bicarbonated spring, a simple thermal spring, a carbon dioxide spring, a radioactive spring or a sulfur spring;

passing fresh water, in the following order, through an activated carbon filter, a microfilter, an anion-exchange resin and a cation-exchange resin to prepare pure water; and mixing the thermal water solution with the pure water and heating the water mixed with thermal water solution to prepare the thermal water prior to distributing the thermal water to a bathtub.

BRIEF DESCRIPTION OF THE DRAWINGS

Other objects and aspects of the invention will become apparent from the following description of embodiments with reference to the accompanying drawings in which.

DETAILED DESCRIPTION OF THE EMBODIMENT

Figure 1:
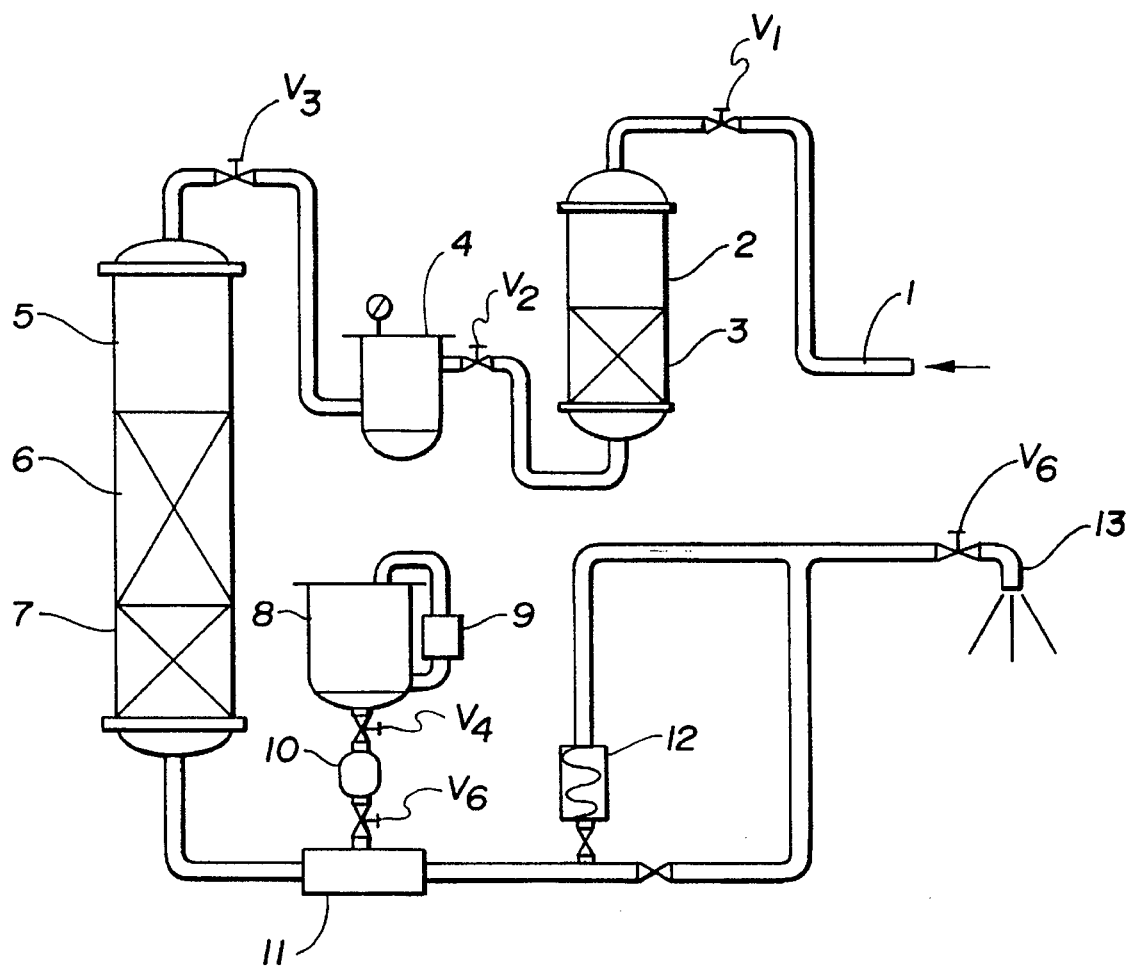
FIG. 1 is a schematic view of a thermal water preparing device suitable for carrying out the method of this invention.

FIG. 1 is a schematic view showing the construction of an artificial thermal water preparing device suitable for carrying out the method of this invention. As shown in this drawing, the artificial thermal water preparing device includes an organic matter filtering section wherein fresh water or city water supplied through a water pipe 1 of a bathroom passes through activated carbon 3 of an activated carbon filter 2. The above organic matter filtering section is followed by a microparticle filtering section wherein the water coming out of the activated carbon filter 2 passes through a microfilter 4 to filter out microparticles. The microparticle filtering section in turn is connected to a pure water preparing section wherein the water coming out of the microfilter 4 passes through a resin tank 5. In the resin tank 5, the water passes, in the following order, through the anion-exchange resin 6 and cation-exchange resin 7. The pure water prepared by the pure water preparing section in turn is distributed to a bathtub from a water tap 13. A thermal water mixing unit is coupled to a pipe extending between the resin tank 5 and the water tap 13. The thermal water mixing unit comprises a thermal water solution tank 8 with a circulation pump 9. The solution tank 8 is coupled to a solution distributing tank 10 with a valve $V_4$ interposed between the solution tank 8 and the solution distributing tank 10. The valve $V_4$ is operated to distribute the thermal water solution from the solution tank 8 to the distributing tank 10. The solution distributing tank 10 in turn is coupled to a mixing tank 11 with a valve $V_5$ interposed between the tanks 10 and 11. This valve $V_5$ is operated to distribute the thermal water solution from the distributing tank 10 to the mixing tank 11. The thermal water solution distributed from the distributing tank 10 is mixed with the pure water in the mixing tank 11. The mixed thermal water is in turn heated by a heater 12 before the thermal water is distributed to the bathtub.

Figure 2:
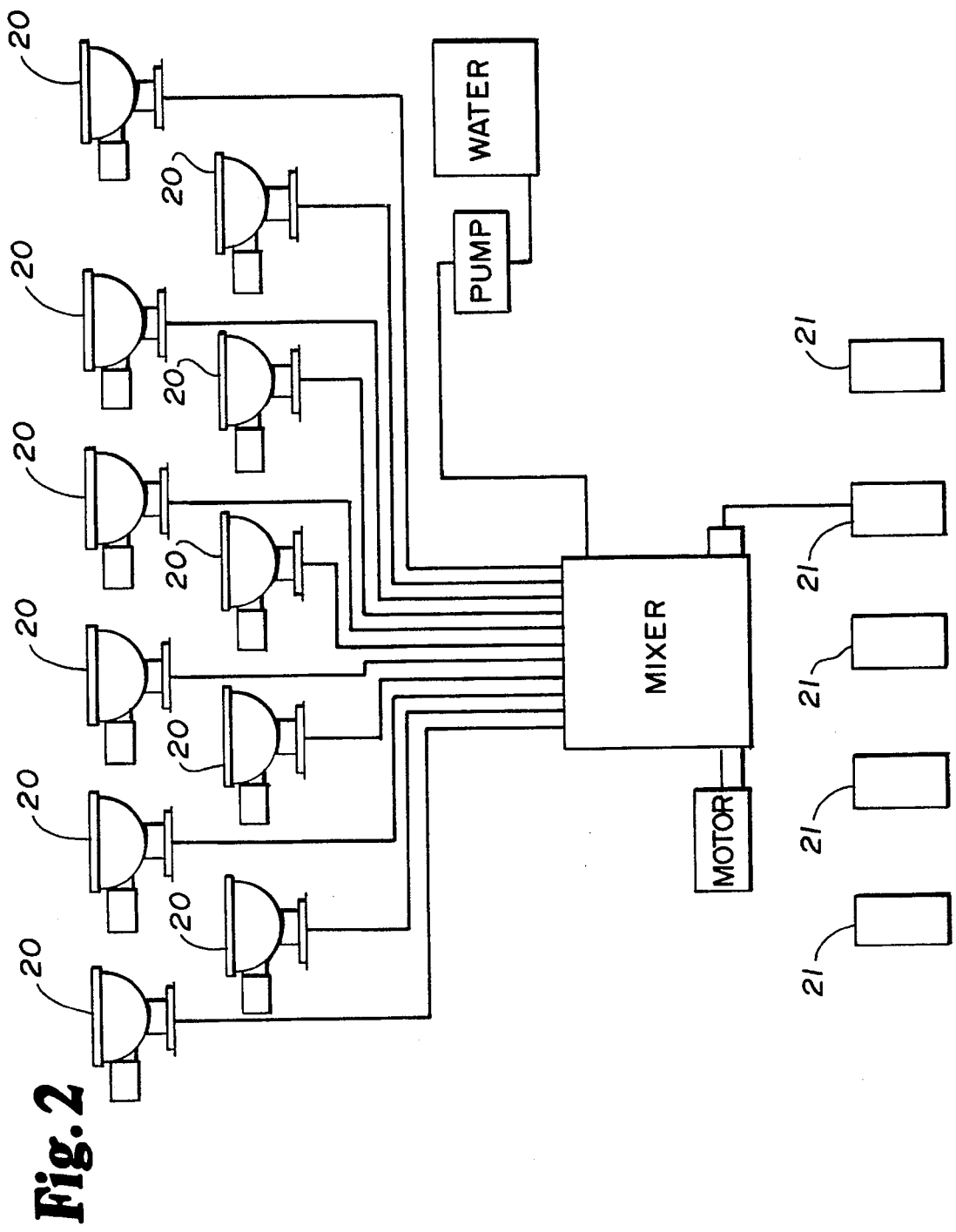
FIG. 2 is a view showing the process for preparing various thermal water solutions to be contained in thermal water solution tanks and selectively mixed with pure water to prepare the artificial thermal water of this invention.

FIG. 2 is a view showing the process for preparing the thermal water solution to be contained in a thermal water solution tank of the above device and mixed with pure water to prepare artificial thermal water according to this invention. As shown in this drawing, eleven kinds of chemicals to be used for preparing the thermal waters according to this invention are each contained in separate chemical containers 20 respectively. In this case, the amount of each chemical contained in each container 20 is the amount to be used for preparing 18,000 l of thermal water about 100 times. In order to prepare the artificial thermal water of this invention, the unit amount of chemicals of the containers 20 to be used for preparing 18,000 l of thermal water once are automatically weighed by an automatic gauge and in turn distributed to a mixer to be mixed with high purity water and thereby becoming a thermal water solution. The above thermal water solution in turn is filled in a 6 l container 21 which will be used as the thermal water solution tank 8 of the device of FIG. 1. In this case, the chemicals, except for powder chemicals, are preferred to be finely ground using a grinder prior to filling the containers 20 with the chemicals.

The process for preparing the thermal water in accordance with the invention will be described in detail hereinbelow.

The fresh water of the water pipe 1 is supplied to the activated carbon filter 2 wherein the fresh water passes through the activated carbon 3 of the filter 2 to filter off the organic matters. The activated carbon 3 also deodorizes the fresh water and absorbs any phenol and benzene from the fresh water. The water coming out of the activated carbon filter 2 in turn passes through the microfilter 4 wherein the microparticles and colloid matters of the water are filtered off. The need for replacing the used microfilter 4 with a new filter may be checked by means of pressure difference. The water coming out of the microfilter 4 in turn is supplied to the resin tank 5. In the resin tank 5, the water passes through recycled ion-exchange resins, that is, the anion-exchange resin 6 and the cation-exchange resin 7. Therefore, the ionic impurities of the water are filtered off in such a manner that the cations and anions are completely absorbed and removed by strong acid-exchange resin and strong basic anion-exchange resin respectively. Highly pure water is thus prepared. The above-mentioned process for preparing the pure water is well known to those skilled in the art. The pure water coming out of the resin tank 5 in turn is mixed with the thermal water solution distributed from the solution tank 8 to form artificial thermal water of this invention.

The pure water coming out of the resin tank 5 is supplied to fill the bathtub through the water tap 13. When the bathtub is filled with the pure water to one third, the thermal water solution is added into the bathtub. In order to add the thermal water solution, the valve $V_4$ is opened to allow the unit amount of thermal water solution (about 20 ml) to be filled in the distributing tank 10. The valve $V_4$ is closed. The unit amount of the thermal water solution refers to the amount to be used for preparing the thermal water once. The thermal water solution of the solution tank 8 has been circulated by the pumping force of the circulation pump 9 and thereby properly mixed. After closing the above valve $V_4$, the next valve $V_5$ is opened to allow the thermal water solution to be discharged from the distributing tank 10 into the mixing tank 11. In the mixing tank 11, the thermal water solution is mixed with the pure water flowing in the mixing tank 11 and thereafter discharged from the pure water tap 13 into the bathtub. In this case, the thermal water is appropriately heated by the heater 12 in accordance with the kinds of the thermal water before the thermal water is discharged from the water tap 13.

In the mixing tank 11, the thermal water solution which has been preliminarily mixed by the pumping force of the circulation pump 9 is mixed again by the vortex of pure water. Therefore, it is possible to prevent either lumping together or deposition of the chemicals and thereby uniformly mixing the thermal water solution with the pure water. Thereafter, the pure water supply continues until the bathtub is fully filled with water. The water in the bathtub thus becomes the artificial thermal water having the appropriate temperature and ingredients.

In accordance with the present invention, various artificial thermal waters can be prepared. In order to prepare various thermal waters, several solution tanks 8 filled with different thermal water solutions may be selectively installed in the thermal water mixing unit.

The chemical components and contents of the various thermal water solutions to be filled in the solution tank 8 of the thermal water mixing unit of this invention will be described along with the chemical components and contents of natural thermal waters in the following examples.

EXAMPLE 1

Sodium bicarbonated spring:

The chief ingredient of this spring is sodium bicarbonate, so that this spring is otherwise referred to as an alkaline spring. 1 Kg of thermal water of this spring includes at least 340 mg of sodium bicarbonate. This spring is a colorless transparent spring. Bathing in this spring removes fats and oil from the skin and thereby refreshes a person in mind and body. The hydrocarbonic acid ion of this spring stimulates the connective tissues of body and thereby promotes cellular regeneration.

This spring is good for female skin beauty, neuralgia, anemia, high blood pressure and diabetes. The characteristics of this spring were analyzed and represented in the following chart. The following chart also shows the chemical components of the thermal water solution for preparing the artificial thermal water of this invention corresponding to the above spring.

| (spring characteristics) | | | |
|---|---|---|---|
| pH: 7.89 | | temperature: | 30°–45° C. |
| solid remains: 129.0 | | | |
| chief ingredient: (unit: mg/l of thermal water): | | | |
| $K^+$: 0.37 | $Na^{++}$: 30.5 | $Ca^{++}$: 7.79 | $Mg^+$: 0.48 |
| Li: 0.05 | $Cl^-$: 8.5 | $SO_4^{--}$: 7.74 | $HCO_3^-$: 43.9 |
| $CO_3^{--}$: 14.4 | $F^-$: 5.0 | $SiO_2$: 15.8 | |

| (chemical components of thermal water solution, unit: g/18,000 l of thermal water) | |
|---|---|
| $CaCO_3$: 358.65 | $MgCl_2 6H_2O$ : 73.188 |
| $Li_2CO_3$: 5.54 | NaCl: 211.64 |
| $NaHCO_3$: 1070.5 | $Na_2SO_4$: 190.61 |
| $SiO_2$: 284.4 | $Na_2CO_3$: 68.24 |
| NaF: 205.0 | $K_2SO_4$: 15.27 |

EXAMPLE 2

Simple thermal spring:

This spring has very simple ingredients and includes at least 250 mg of free carbonic acid and at least 100 mg of vaporization remains in 1 Kg of thermal water. This spring is a colorless, transparent, tasteless and odorless spring and soft to give less stimulus to body and thereby being suitable to older people.

This spring is good for promotion of blood generation, neuralgia, rheumatic troubles, skin disease and recuperation after illness. The characteristics of this spring were analyzed and represented in the following chart. The following chart also shows the chemical components of thermal water solution for preparing the artificial thermal water of this invention corresponding to the above spring.

| (spring characteristics) | | | |
|---|---|---|---|
| pH: 9.01 | | temperature: | 40°–45° C. |
| solid remains: 178.5 | | | |
| chief ingredient: (unit: mg/l of thermal water): | | | |
| $K^+$: 1.90 | $Na^{++}$: 48.0 | $Ca^{++}$: 4.00 | $Mg^+$: 0.24 |
| Li: 0.06 | $Cl^-$: 18.8 | $SO_4^{--}$: 12.4 | $HCO_3^-$: 82.0 |
| $CO_3^{--}$: 7.79 | $F^-$: 7.0 | $SiO_2$: 25.3 | |

| (spring characteristics) |
| --- |
| (chemical components of thermal water solution, unit: g/18,000 l of thermal water) |
| $CaCO_3$: 180.0     $MgCl_2 6H_2O$: 33.54 |
| $Li_2CO_3$: 6.48     NaCl: 538.88 |
| $NaHCO_3$: 1999.74     $Na_2CO_4$: 264.27 |
| $SiO_2$: 456.0     $Na_2CO_3$: 27.76 |
| NaF: 280.0     $K_2SO_4$: 76.18 |

EXAMPLE 3

Carbon dioxide spring:

This spring includes at least 1000 mg of free carbonic acid in 1 Kg of thermal water. This spring is a colorless transparent spring and has an acid taste and the taste of soda pop. As this spring generates small carbonic acid gas bubbles innumerable, this spring is otherwise stated as a "bubble spring."

This spring is good for blood circulation, developing an appetite, heart acceleration, urinary diseases and impotency. The characteristics of this spring were analyzed and represented in the following chart. The following chart also shows the chemical components of thermal water solution for preparing the artificial thermal water of this invention corresponding to the above spring.

| (spring characteristics) |
| --- |
| pH: 9.15     temperature: 40°–55° C. |
| solid remains: 194.5 |
| chief ingredient: (unit: mg/l of thermal water): |
| $K^+$: 1.90    $Na^{++}$: 59.5    $Ca^{++}$: 1.40    $Mg^+$: 0.12 |
| Li: 0.05    $Cl^-$: 39.5    $SO_4^{--}$: 9.22    $HCO_3^-$: 61.5 |
| $CO_3^{--}$: 21.6    $F^-$: 2.2    $SiO_2$: 32.5 |

| (chemical components of thermal water solution, unit: g/18,000 l of thermal water) |
| --- |
| $CaCO_3$: 63.0     $MgCl_2 6H_2O$: 18.29 |
| $Li_2CO_3$: 5.40     NaCl: 1160.97 |
| $NaHCO_3$: 1124.24     $Na_2SO_4$: 180.80 |
| $SiO_2$: 585.0     $Na_2CO_3$: 432.12 |
| NaF: 88.0     $K_2SO_4$: 76.18 |

EXAMPLE 4

Radioactive spring:

This spring includes at least 82.5 mg of radon in 1 Kg of thermal water and thus otherwise stated as a "radon spring." This spring is a colorless, tasteless, odorless and soft spring. This spring is good for skin disease, neuralgia, gastroenteric disorder, fatness, diabetes and women's diseases. The characteristics of this spring were analyzed and represented in the following chart. The following chart also shows the chemical components of thermal water solution for preparing the artificial thermal water of this invention corresponding to the above spring.

Please note that a person having a weak mucous membrane should avoid bathing in this spring.

| (spring characteristics) |
| --- |
| pH: 8.89     temperature: 42°–55° C. |
| solid remains: 180.5 |
| chief ingredient: (unit: mg/l of thermal water): |
| $K^+$: 1.50    $Na^{++}$: 48.5    $Ca^{++}$: 1.80    $Mg^+$: 0.12 |
| Li: 0.11    $Cl^-$: 20.5    $SO_4^{--}$: 9.05    $HCO_3^-$: 76.1 |
| $CO_3^{--}$: 8.63    $F^-$: 5.5    $SiO_2$: 28.0    Fe: 0.01 |

| (chemical components of thermal water solution, unit: g/18,000 l of thermal water) |
| --- |
| $CaCO_3$: 81.0     $MgCl_2 6H_2O$: 18.29 |
| $Li_2CO_3$: 11.88     NaCl: 398.03 |
| $NaHCO_3$: 1855.85     $Na_2SO_4$: 163.33 |
| $SiO_2$: 504.0     $Na_2CO_3$: 167.85 |
| NaF: 220.0     $K_2SO_4$: 60.14 |
| $FeCl_3 6H_2O$: 0.935 |

EXAMPLE 5

Sulfur spring:

This spring includes at least 1.0 mg of sulfur in 1 Kg of thermal water. The thermal water of this spring is a white and muddy water and gives off an odor like as the smell of rotten egg. This spring is good for arteriosclerosis, frostbite, counteracting poison, neuralgia, and promotion of vitality. The characteristics of this spring were analyzed and represented in the following chart. The following chart also shows the chemical components of a thermal water solution for preparing the artificial thermal water according to this invention corresponding to the above spring.

Please note that the above spring is not suitable for weak or older people. Additionally, a person having either oversensitive mucous membrane or oversensitive skin should avoid bathing in this spring. Furthermore, the bathroom should be ventilated.

| (spring characteristics) |
| --- |
| pH: 9.43     temperature: 42°–52° C. |
| solid remains: 176.0 |
| chief ingredient: (unit: mg/l of thermal water): |
| $K^+$: 0.99    $Na^{++}$: 4.40    $Ca^{++}$: 1.59    $Mg^+$: 0.10 |
| Li: 0.05    $Cl^-$: 12.4    $SO_4^{--}$: 14.1    $HCO_3^-$: 29.3 |
| $CO_3^{--}$: 25.9    $F^-$: 2.4    $SiO_2$: 40.8    Fe: 0.11 |

| (chemical components of thermal water solution, unit: g/18,000 l of thermal water) |
| --- |
| $CaCO_3$: 71.55     $MgCl_2 6H_2O$: 15.24 |
| $Li_2CO_3$: 5.54     NaCl: 352.83 |
| $NaHCO_3$: 714.54     $Na_2SO_4$: 338.23 |
| $SiO_2$: 734.40     $Na_2CO_3$: 167.85 |
| NaF: 96.0     $K_2SO_4$: 39.69 |
| $FeCl_3 6H_2O$: 10.29 |

The above-mentioned thermal water solutions for preparing various artificial thermal waters corresponding to the various natural springs according to this invention are charged in solution tanks 8. The solution tanks 8 filled with the thermal water solutions are selectively installed in the thermal water mixing unit of FIG. 1 and thereby easily prepare the artificial thermal water.

In order to more easily carry out the present invention, the thermal water preparing device of FIG. 1 may be installed in an automatic system. In this case, the valve operation, sensing of thermal water temperature, checking of both the filter changing time and the ion-exchange resin recycling time and displaying of the amount of remaining thermal water solution may be automatically performed.

As described above, the artificial thermal water preparing method of this invention overcomes the problems caused when using naturally occurring thermal waters, which are not sufficiently popularized due to several causes. The method of this invention mixes thermal water solutions with pure water prepared by the pure water preparing device, thus to readily prepare the artificial thermal waters suitable to be used for domestic thermal-water bathing.

Although the preferred embodiments of the present invention have been disclosed for illustrative purposes, those skilled in the art will appreciate that various modifications, additions, and substitutions are possible, without departing from the scope and spirit of the invention as disclosed in the accompanying claims.

What is claimed is:

1. A method for preparing thermal water comprising the steps of:

mixing a plurality of thermal water solutions, each thermal water solution made up by mixing a plurality of chemical components with highly pure water at predetermined rates to prepare thermal water solutions having components similar to those of a natural sodium bicarbonated spring, a simple thermal spring, a carbon dioxide spring, a radioactive spring or a sulfur spring;

providing each of the plurality of thermal water solutions within its own solution tank;

in order, passing fresh water through an activated carbon filter, a microfilter, an anion-exchange resin and a cation-exchange resin to prepare pure water, and running the pure water into a mixing chamber;

selecting one of the plurality of thermal water solutions for making the thermal water to be distributed and directing the thermal water solution from a selected solution tank to the mixing chamber with the pure water; and mixing the thermal water solution with the pure water within the mixing chamber, heating the water mixed with the thermal water solution to prepare the thermal water, and therafter distributing the water mixed with the thermal water solution to a bathtub.

2. The method according to claim 1, wherein the amount in grams of chemical components of the thermal water solution for preparing 18,000 l of thermal water corresponding to the natural sodium bicarbonated spring is as follows:

| | |
|---|---|
| $CaCO_3$: 358.65 | $MgCl_2 6H_2O$: 73.188 |
| $Li_2CO_3$: 5.54 | NaCl: 211.64 |
| $NaHCO_3$: 1070.5 | $Na_2SO_4$: 190.61 |
| $SiO_2$: 284.4 | $Na_2CO_3$: 68.24 |
| NaF: 205.0 | $K_2SO_4$: 15.27. |

3. The method according to claim 1, wherein the amount in grams of chemical components of thermal water solution for preparing 18,000 l of thermal water corresponding to the natural simple thermal spring is as follows:

| | |
|---|---|
| $CaCO_3$: 180.00 | $MgCl_2 6H_2O$: 33.54 |
| $Li_2CO_3$: 6.48 | NaCl: 538.88 |
| $NaHCO_3$: 1999.74 | $Na_2SO_4$: 264.27 |
| $SiO_2$: 456.0 | $Na_2CO_3$: 27.76 |
| NaF: 280.0 | $K_2SO_4$: 76.18. |

4. The method according to claim 1, wherein the amount in grams of chemical components of the thermal water solution for preparing 18,000 l of thermal water corresponding to the natural carbon dioxide spring is as follows:

| | |
|---|---|
| $CaCO_3$: 63.0 | $MgCl_2 6H_2O$: 18.29 |
| $Li_2CO_3$: 5.40 | NaCl: 1160.97 |
| $NaHCO_3$: 1124.24 | $Na_2SO_4$: 180.80 |
| $SiO_2$: 585.0 | $Na_2CO_3$: 432.12 |
| NaF: 88.0 | $K_2SO_4$: 76.18. |

5. The method according to claim 1, wherein the amount in grams of chemical components of the thermal water solution for preparing 18,000 l of thermal water corresponding to the natural radioactive spring is as follows:

| | |
|---|---|
| $CaCO_3$: 81.0 | $MgCl_2 6H_2O$: 18.29 |
| $Li_2CO_3$: 11.88 | NaCl: 398.03 |
| $NaHCO_3$: 1855.85 | $Na_2SO_4$: 163.33 |
| $SiO_2$: 504.0 | $Na_2CO_3$: 167.85 |
| NaF: 220.0 | $K_2SO_4$: 60.14 |
| $FeCl_3 6H_2O$: 0.935. | |

6. The method according to claim 1, wherein the amount in grams of chemical components of the thermal water solution for preparing 18,000 l of thermal water corresponding to the natural sulfur spring is as follows:

| | |
|---|---|
| $CaCO_3$: 71.55 | $MgCl_2 6H_2O$: 15.24 |
| $Li_2CO_3$: 5.54 | NaCl: 352/83 |
| $NaHCO_3$: 714.54 | $Na_2SO_4$: 338.23 |
| $SiO_2$: 734.40 | $Na_2CO_3$: 167.85 |
| NaF: 96.0 | $K_2SO_4$: 39.69 |
| $FeCl_3 6H_2O$: 10.29. | |

\* \* \* \* \*